(12) United States Patent
Choung et al.

(10) Patent No.: US 10,016,400 B2
(45) Date of Patent: Jul. 10, 2018

(54) COMPOSITION INCLUDING RAPAMYCIN AS ACTIVE INGREDIENT FOR PREVENTING OR TREATING HEARING LOSS

(71) Applicant: AJOU UNIVERSITY INDUSTRY—ACADEMIC COOPERATION FOUNDATION, Suwon-si, Gyeonggi-do (KR)

(72) Inventors: Yun-Hoon Choung, Seoul (KR); Yeon Ju Kim, Suwon-si (KR)

(73) Assignee: AJOU UNIVERSITY INDUSTRY-ACADEMIC COOPERATION FOUNDATION, Suwon-si, Gyeonggi-do (KR)

(*) Notice: Subject to any disclaimer, the term of this patent is extended or adjusted under 35 U.S.C. 154(b) by 1 day.

(21) Appl. No.: 14/876,826

(22) Filed: Oct. 7, 2015

(65) Prior Publication Data

US 2016/0101088 A1    Apr. 14, 2016

(30) Foreign Application Priority Data

Oct. 8, 2014    (KR) .................. 10-2014-0135880

(51) Int. Cl.
*A61K 31/436*    (2006.01)
*A61K 31/7036*    (2006.01)
*A23L 33/10*    (2016.01)

(52) U.S. Cl.
CPC ............ *A61K 31/436* (2013.01); *A23L 33/10* (2016.08); *A61K 31/7036* (2013.01)

(58) Field of Classification Search
CPC .... A61K 31/436; A61K 31/7036; A23L 33/10
See application file for complete search history.

(56) References Cited

PUBLICATIONS

Definition of prevent, Oxford English Dictionary Online, http://dictionary.oed.com/, accessed online Mar. 27, 2010, especially definition 9a. at p. 2.*
Hearing Loss Association of America website, http://www.hearingloss.org/content/symptoms-hearing-loss, accessed online on Dec. 19, 2016.*
Cui et al., Scientific Reports, 2015, 5, p. 1-17, published online: Jun. 8, 2015.*
Menardo et al., Antioxid. Redox Signaling, 2012, 16(3), p. 263-274.*
Ladrech et al., J. Neurosci. Res., 2007, 85, p. 1970-1979.*
Harrison et al., Nature, 2009, 460, p. 392-395 and methods page.*
Bin Fang et al., "Rapamycin alleviates cisplatin-induced ototoxicity in vivo", Biochemical and Biophysical Research Communications 448 (2014) 443-447.

* cited by examiner

*Primary Examiner* — Jonathan S Lau
(74) *Attorney, Agent, or Firm* — Revolution IP, PLLC (57) ABSTRACT

A pharmaceutical or health food includes rapamycin as an active ingredient, the pharmaceutical or health food being applied for prevention, improvement, and treatment of ototoxic hearing loss caused by an aminoglycoside-based antibiotic, sudden sensorineural hearing loss, and noise induced hearing loss. The pharmaceutical or health food is also applied to a pharmaceutical composite preparation of an aminoglycoside-based antibiotic and rapamycin, the pharmaceutical composite preparation reducing a side effect of the aminoglycoside-based antibiotic.

4 Claims, 5 Drawing Sheets

COMPOSITION INCLUDING RAPAMYCIN AS ACTIVE INGREDIENT FOR PREVENTING OR TREATING HEARING LOSS

CROSS-REFERENCE TO RELATED PATENT APPLICATION

This application claims the benefit of Korean Patent Application No. 10-2014-0135880 filed on Oct. 8, 2014, in the Korean Intellectual Property Office, the disclosure of which is incorporated herein in its entirety by reference.

BACKGROUND

The present disclosure relates to a composition for preventing or treating ototoxic hearing loss, sudden sensorineural hearing loss, and noise induced hearing loss that are caused by aminoglycoside-based antibiotic.

Hearing loss, which is also known as deafness, can be divided into conducive hearing loss and sensorineural hearing loss. The conducive hearing loss occurs when an external ear and a middle ear, which are organs responsible for transmission of sound, are infected with a disease such as inflammation, and the sensorineural hearing loss occurs when problems arise in a cochlea that is an organ responsible for detection of sound, auditory nerves that transmit sound into electric energy, and a brain that is an organ responsible for hearing and performs comprehensive roles including discrimination and understand of sound. Hearing loss is a common disease that appears in about 15 to about 20% of the population. In particular, the sensorineural hearing loss may be caused by an inflammatory disease, such as labyrinthitis or meningitis, noise, an ototoxic drug, an injury, such as a fracture of a temporal bond, presbycusis, a Meniere's disease, a disease associated with a metabolism, such as hypothyroidism, an ischemic brain disease, a blood disease, such as leukemia, neurological indisposition, such as multiple sclerosis, an immune disorder, a tumoral disease, such as acoustic tumor, or a bone disease.

An aminoglycoside-based antibiotic is one of representative ototoxic drugs, and examples thereof include streptomycin, kanamycin, gentamicin, neomycin, amikacin, tobramycin, netilmicin, dibekacin, and sisomycin. The aminoglycoside-based antibiotic is mainly used for gram-negative infection, which is not influenced by typical antibiotics, tuberculosis, or deep wound infection. The aminoglycoside-based antibiotic may have ototoxicity that causes dysfunction of hearing loss and balance in an inner ear, and side effects of nephrotoxicity. Such ototoxicity and side effects may occur when a subject takes an overdose of a drug or takes a drug for a long period of time. In some cases, ototoxicity may be also caused when a subject takes an appropriate dose of a drug for a short period of time. The ototoxicity of the aminoglycoside-based antibiotic is shown as a disorder of vestibular function in about 15% of users, and as hearing loss in about 10 to about 30% of users. In particular, the ototoxicity of the aminoglycoside-based antibiotic occurs in both ears in a form of severe hearing loss at a high frequency of about 4,000 hertz (Hz). Studies attempted to prevent and treat ototoxic hearing loss were mainly focused on antioxidant therapy having protective effects using an antioxidant. Here, it has been reported that vitamin E, aspirin, and N-acetylcysteine were found to be effective in reducing ototoxicity caused by the aminoglycoside-based antibiotic. However, it has been also reported that aspirin had adverse effects in promoting ototoxicity, or had problems in causing severe side effects on other organs.

An endoplasmic reticulum (ER) called an autophagosome is recently observed in a hair cell, and accordingly, an autophagy phenomenon and a correlation between the autophagosome and ototoxicity come into the spotlight. Rapamycin (RPM) is known to serve to block functions of a mammalian target of rapamycin (mTOR) which controls various factors involved in cell growth and division, and accordingly to induce autophagy, which is a new type of an apoptosis mechanism upon down-regulation of proteins of autophagy-related genes (Atg). Thus, RPM has been widely used as a representative autography inducer.

Thus, RPM receives the attention in studies for ototoxicity, and recently, relaxation effects of RPM against ototoxicity caused by an anticancer drug, cisplatin, have been disclosed (refer to non-patent document 1).

It is similar that both aminoglycoside and cisplatin are associated with ototoxicity upon generation of reactive oxygen species (ROS). However, in the case of aminoglycoside, it is known that aminoglycoside enters into auditory cells through a mechano-electrical transducer (MET) channel to be combined with iron ($Fe^{2+}$), and accordingly, an aminoglycoside-$Fe^{2+}$ complex obtained therefrom induces formation of ROS while causing damages to the auditory cells only.

However, in the case of cisplatin, it is known that cisplatin forms a monohydrate complex which generates nicotinamide adenine dinucleotide phosphat-oxidase 3 (NADPH oxidase 3, NOX-3), and accordingly, ROS is produced very excessively so that not only the auditory cells, but also surrounding support cells and nerve cells are also influenced by ROS. In addition, it has been reported that cisplatin induces apoptosis through a caspase-dependent pathway while aminoglycoside induces apoptosis through both a caspase-dependent pathway and a caspase-independent pathway. Regarding the occurrence of symptoms, auditory abnormalities appear with a delay for about a few days or weeks to a patient subjected to administration of aminoglycoside-based antibiotics. However, auditory abnormalities appear relatively quickly to a patient subjected to administration of cisplatin. Since there is obvious differences in the mechanism of ototoxicity between the two drugs, it cannot conclude that the drugs are preferable therapeutics for ototoxic hearing loss caused by the aminoglycoside-based antibiotic.

Therefore, the effects of the RPM on the ototoxic hearing loss caused by the aminoglycoside-based antibiotics need to be confirmed.

PRIOR ART DOCUMENT

Patent document

1. BBRC Volume 448, 13 Jun. 2014, 443-447.

SUMMARY

Provided is a pharmaceutical composition including rapamycin as an active ingredient for preventing or treating hearing loss.

Provided is a health food including rapamycin as an active ingredient for preventing or treating hearing loss.

Additional aspects will be set forth in part in the description which follows and, in part, will be apparent from the description, or may be learned by practice of the presented exemplary embodiments.

According to an aspect of an exemplary embodiment, there is provided a pharmaceutical composition including rapamycin as an active ingredient for preventing or treating hearing loss selected from ototoxic hearing loss caused by an aminoglycoside-based antibiotic, sudden sensorineural hearing loss, and noise induced hearing loss.

According to an aspect of another exemplary embodiment, there is provided a health food including rapamycin as an active ingredient for preventing or treating hearing loss selected from ototoxic hearing loss caused by an aminoglycoside-based antibiotic, sudden sensorineural hearing loss, and noise induced hearing loss.

BRIEF DESCRIPTION OF THE DRAWINGS

These and/or other aspects will become apparent and more readily appreciated from the following description of the exemplary embodiments, taken in conjunction with the accompanying drawings in which:

FIGS. 1A and 1B illustrates graphs showing results of an auditory brainstem response (ABR) test, wherein

DETAILED DESCRIPTION

Reference will now be made in detail to exemplary embodiments, examples of which are illustrated in the accompanying drawings, wherein like reference numerals refer to like elements throughout. In this regard, the present exemplary embodiments may have different forms and should not be construed as being limited to the descriptions set forth herein. Accordingly, the exemplary embodiments are merely described below, by referring to the figures, to explain aspects. Expressions such as "at least one of," when preceding a list of elements, modify the entire list of elements and do not modify the individual elements of the list.

Hereinafter, the present inventive concept will be described in detail.

The present inventors have completed the present inventive concept as follows: administration of a combination of rapamycin (RPM) and a representative aminoglycoside-based antibiotic, gentamicin (GT), results in reduction of hearing loss and damages to auditory outer hair cells; administration of GT only results in increased number of autophagosomes having a double membrane in auditory outer and inner hair cells; administration of a combination of GT and RPM results in reduction of apoptosis; and administration of GT and an autophagy inhibitor, chloroquine (CQ), results in increased apoptosis.

The aminoglycoside-based antibiotic may include at least one selected from amikacin, arbekacin, gentamicin, kanamycin, neomycin, netilmicin, paromomycin, dibekacin, sisomicin, streptomycin, and tobramycin, but is not limited thereto.

RPM is a substance separated from *Streptomyces hygroscopicus* which is a soil bacterium living in the Polynesia Easter Island in the South Pacific Ocean. RPM is known to serve to block functions of a mammalian target of rapamycin (mTOR) which controls various factors involved in cell growth and division, and accordingly to induce autophagy, which is a new type of an apoptosis mechanism upon down-regulation of proteins of autophagy-related genes (Atg). Thus, RPM has been widely used as a representative autography inducer.

Autophagy, as being in a new form associated with cell survival and apoptosis, involves ceaseless processes of death and regeneration of organelles in a different manner from apoptosis or necrosis in which the whole cells become extinct. Through these processes in autophagy, cellular damages are removed while a cellular structure is re-established. Accordingly, cells that are fed back with proteins and intracellular nutrients and energy required for survival are adapted to a stressed environment and regain homeostasis.

Therefore, the present inventive concept provides pharmaceutical composition including RPM as an active ingredient for preventing and treating hearing loss selected from the group consisting of ototoxic hearing loss caused by an aminoglycoside-based antibiotic, sudden sensorineural hearing loss, and noise induced hearing loss.

The pharmaceutical composition may further include at least one adjuvant selected from the group consisting of carriers, excipients, disintegrating agents, sweetening agents, coating agents, swelling agents, lubricants, glidants, flavoring agents, antioxidants, buffer solutions, bacteriostatic agents, diluents, dispersants, surfactants and binders.

In detail, examples of carriers, excipients, and diluents may include lactose, dextrose, sucrose, sorbitol, mannitol, xylitol, erythritol, maltitol, starch, acacia rubber, alginate, gelatin, calcium phosphate, calcium silicate, cellulose, methyl cellulose, microcrystalline cellulose, polyvinylpyrrolidone, water, methyl hydroxybenzoate, propyl hydroxybenzoate, talc, magnesium stearate, and mineral oil. Examples of solid preparation for oral administration may include tablets, pills, powders, granules, or capsules. Such solid preparation may be prepared by mixing with the pharmaceutical composition with at least one of excipients, for example, starch, calcium carbonate, sucrose or lactose, or gelatin. In addition, lubricants, such as magnesium stearate and talc, other than simple excipients, may be also used for prepare solid preparation. Examples of liquid preparation for oral administration may include, liquid formulation for internal application, emulsions, or syrups. Various excipients, such as wetting agents, sweeteners, aromatics, and preservatives, may be included in the preparation in addition simple diluents, such as water or liquid paraffin, that are simply generally used in the art. Examples of preparation for parenteral administration may include sterile aqueous solutions, non-aqueous solvents, suspensions, emulsions, freeze-dried preparation, or suppository. Examples of non-aqueous solvents and suspensions may include propylene glycol, polyethylene glycol, vegetable oil, such as olive oil, or injectable ester, such as ethyl oleate. Examples of suppository may include witepsol, macrogol, tween 61, cacao butter, laurinum, or glycerogelatin.

The pharmaceutical composition according to the present inventive concept may be formulated in a conventional manner as powders, granules, tablets, capsules, suspensions, emulsions, syrups, oral dosage forms including aerosol, external preparation, suppository, and sterile injectable solutions.

When being formulated, fillers, extenders, binders, wetting agents, disintegrating agents, diluents including surfactants, or excipients, which are generally used in the art, may be used for preparations. Examples of solid preparation for oral administration may include tablets, pills, powders, granules, or capsules. Such solid preparation may be prepared by mixing with the pharmaceutical composition with at least one of excipients, for example, starch, calcium carbonate, sucrose or lactose, or gelatin.

In addition, lubricants, such as magnesium stearate and talc, other than simple excipients, may be also used for prepare solid preparation. Examples of liquid preparation for oral administration may include suspensions, liquid formulation for internal application, emulsions, or syrups. Various excipients, such as wetting agents, sweeteners, aromatics, and preservatives, may be included in the preparation in addition simple diluents, such as water or liquid paraffin, that are simply generally used in the art.

Examples of preparation for parenteral administration may include sterile aqueous solutions, non-aqueous solvents, suspensions, emulsions, freeze-dried preparation, or suppository. Examples of non-aqueous solvents and suspensions may include propylene glycol, polyethylene glycol, vegetable oil, such as olive oil, or injectable ester, such as ethyl oleate. Examples of suppository may include witepsol, macrogol, tween 61, cacao butter, laurinum, or glycerogelatin.

An amount of RPM, which is the active ingredient of the pharmaceutical composition according to the present inventive concept, may vary depending on a patient's age, gender, weight, and a type of disease, but may be in a range of about 0.001 to about 100 mg/kg, and preferable about 0.01 to about 10 mg/kg. Such an amount of RPM may be administered once a day or several times a day.

In addition, a dosage of RPM according to the present inventive concept may be increased or decreased according to administration routes, severity of disease, or a patient's gender, weight, or age. Thus, the dosage is not construed to limit the scope of the present inventive concept in any aspect.

The pharmaceutical composition may be administered by a variety of routes to rats, mice, domestic animals, and mammals including humans. Any method of administration may be expected, and for example, the pharmaceutical composition may be administered by oral, rectal or intravenous, muscle, subcutaneous, intrauterine duramater, or intracerebroventricular injection, or endobronchotracheal inhalation.

RPM used herein is a chemical having a LD50 value (i.e., a dose lethal to 50% of the population) of at least 2 g/kg, and can be used in the pharmaceutical composition according to the present inventive concept.

In addition, there is provided a pharmaceutical composite preparation including an aminoglycoside-based antibiotic and RPM, characterized by a capability of reducing a side effect of the aminoglycoside-based antibiotic.

The pharmaceutical composite preparation may include the aminoglycoside-based antibiotic and RPM in a range of about 0.01 to about 90 parts by weight, e.g., about 0.1 to about 90 parts by weight, about 1 to about 90 parts by weight, or about 10 to about 90 parts by weight, based on 100 parts by weight of the total preparation, but the embodiment is not limited thereto and may vary according to a patient's condition and a type and progress of the disease.

In addition, there is provided a health food for preventing or improving hearing loss, wherein the health food includes RPM as an active ingredient and the hearing loss is selected from the group consisting of ototoxic hearing loss caused by the aminoglycoside-based antibiotic, sudden sensorineural hearing loss, and noise induced hearing loss.

The health food may be provided in the form of powders, granules, tablets, capsules, syrup or beverage. The health food may be used in combination with other foods or food additives, in addition to the active ingredient, RPM. Such other foods or food additives may be appropriately used in a conventional manner. A mixing amount of the active ingredient may be appropriately determined according to a usage purpose, e.g., prevention, health, or therapeutic treatment.

An effective capacity of RPM included in the health food may be determined based on an effective dose of the pharmaceutical composition, but may be less than the effective dose of the pharmaceutical composition depending on the health or hygiene purposes or in the case of long-term administration for the purpose of health control. Since the active ingredient has no particular problem regarding safety, it is confirmed that the active ingredient can be used in an amount more than the above-described range.

Types of the health food are not particularly limited, and examples thereof are meet, sausages, breads, chocolates, candies, snacks, cookies, pizza, ramen and other noddle types, gums, dairy products including ice cream, various soups, beverages, tea, drinks, alcohol drinks, and vitamin complex.

Hereinafter, the present inventive concept will be described in further detail with reference to the following examples. These examples are for illustrative purposes only and are not intended to limit the scope of the present inventive concept.

EXAMPLE 1

1) Preparation of a Mouse Having Ototoxic Hearing Loss

As an animal model having ototoxic hearing loss, a 7-week-old male Sprague-Dawley rat (SD-rat) to which 220 mg/kg of a representative aminoglycoside-based antibiotic, gentamicin, was administered was used, wherein the administration was performed once a day for 5 days.

A total of 24 rats were classified into one group of 12 rats treated with 50 pM of rapamycin (RRM) and another group of 12 rats treated with 100 pM of RPM. The RPM treatment was carried out once a day for 2 days before carrying out intraperitoneal administration of gentamicin (GM). Afterwards, the RPM treatment was carried out 2 more times in combination with gentamicin. The administration of RPM was carried out according to intratympanic injection through antero-superior portion of a tympanic membrane. To allow RPM to be well absorbed inside the tympanum, the rats were placed in a lateral decubitus position and stabilized. Meanwhile, rats of which right ears were treated with physiological saline were classified as a control group.

2) Preparation of Suditory Cell Line

An auditory cell line, e.g., House-Ear Institute-organ of Corti 1 (HEI-OC1), that expresses auditory genes was used. HEI-OC1 cells were cultured under conditions of a temperature of 33° C. and a $CO_2$ (10%) by adding 10% fetal bovine serum (FBS) and 25 U/ml interferon-gamma to a Dulbecco's modified Eagle's Medium (DMEM) including high concentrations of glutamine. At about 90% confluence of the cultured cells on a bottom surface of a plate, the cell density was maintained within an appropriate range by performing serial subcultures using 2.5% Trypsin-EDTA.

EXAMPLE 2

Auditory Brainstem Response (ABR) Test

To evaluate auditory acuity of the SD-rats of Example 1, an auditory brainstem response (ABR) test was carried out. The ABR test determines an auditory threshold based on minimum stimulation tone (dB) where a wave I or II wavy pattern appeared upon tone-bursts at 16 kHz and 32 kHz by using an ABR device (available from Tucker-Davis Technologies), The auditory acuity was measured one day before drug administration and after the drug administration. Then, RPM (50 pM and 100 pM) was administered to a left ear and 220 mg/kg of GM-containing physiological saline was administered to a right ear, and after 10 days, the same ABR test was carried out again to analyze auditory functions associated with effects of the RPM, and the results are shown in FIGS. 1A and 1B.

Figure 1A:
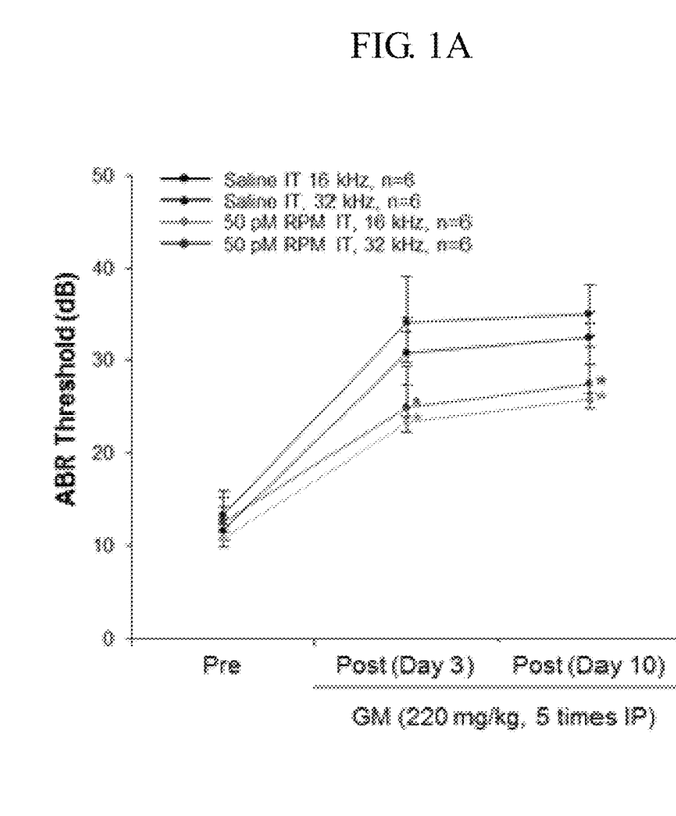
FIG. 1A shows results obtained in a case where 0.5 pM of rapamycin (RPM) is administered.
Figure 1B:
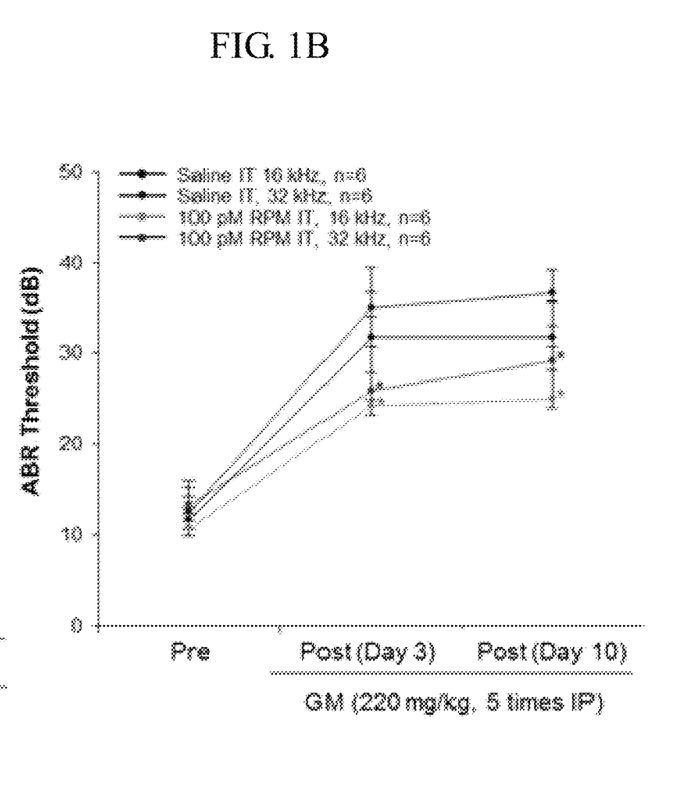
FIG. 1B shows results obtained in a case where 100 pM of RPM is administered.

Referring to FIGS. 1A and 1B, the results obtained by measuring auditory thresholds at 16 KHz and 32 KHz according to the ABR test showed an increased in the auditory thresholds after 3 to 10 days of the GM treatment. However, it was confirmed that the group of rats treated with RPM (at a respective concentration of 50 pM and 100 pM) showed a significant decreased in the auditory thresholds as compared with the control group. Accordingly, it is deemed that the RPM protects ototoxic hearing loss.

EXAMPLE 3

Form Analysis of Cochlea

To analyze a form of the cochlea, the loss and damage of the auditory cells in the cochleae of the rats of Example 1 were evaluated at a basal turn (32 kHz) and a medial turn (16 kHz) by using a scanning electron microscope (SEM). The analysis results are shown in FIG. 2.

Figure 2:
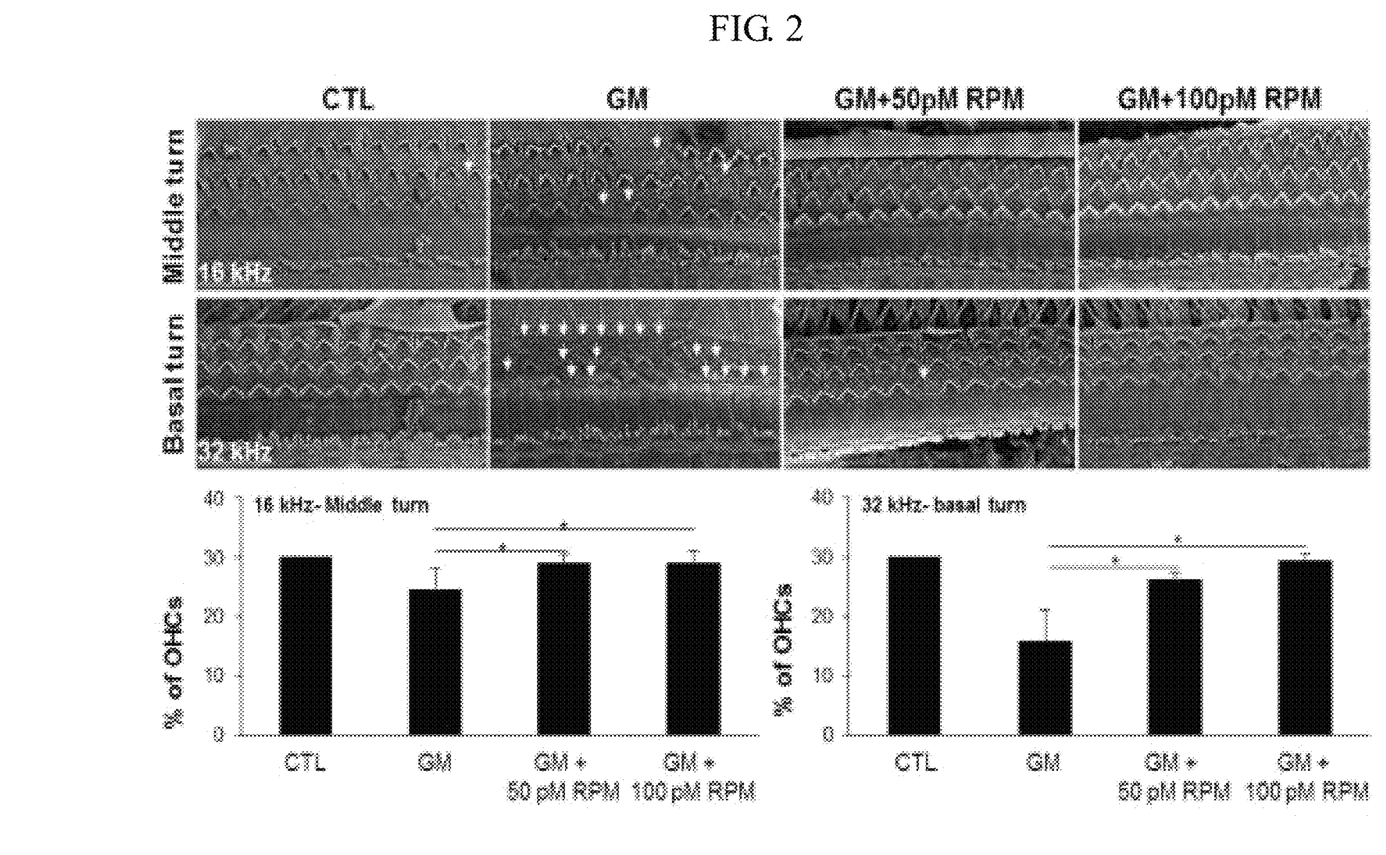
FIG. 2 shows images for analyzing a shape of auditory outer hair cells.

Referring to FIG. 2, in the SEM analysis, the damage of auditory outer hair cells (see white arrows) was observed multiple times in the cochleae of the GM-treated rats compared to the control group at a basal turn (32 kHz) and a medial turn (16 kHz). Meanwhile, it was observed that the auditory outer hair cells were preserved statistically significantly in the cochleae of the RPM-treated rats. Accordingly, it was deemed that the RPM served to protect the auditory cells from being damaged by an ototoxic drug.

EXAMPLE 4

Confirmation of Autophagy in Auditory Outer Hair Cells

To observe autophagy in the auditory outer hair cells, the cochleae of the rats of Example 1 were subjected to immunohistochemistry using microtubule-associated LC3 (Microtubule-associated protein 1A/1B-light chain 3) antibodies. The results are shown in FIG. 3.

Figure 3:
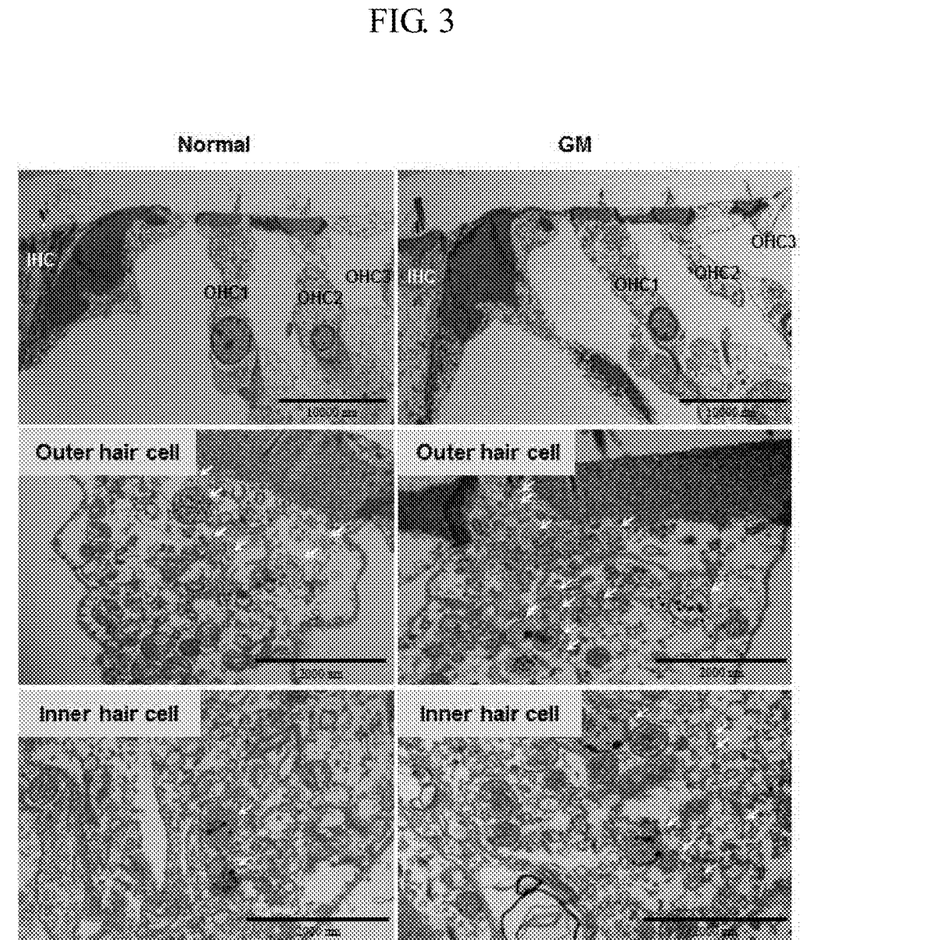
FIG. 3 shows images for determining autophagy in auditory outer hair cells.

Referring to FIG. 3, it was confirmed that the GM treatment led to an increase in autophagosomes each having a double membrane (see white arrows) in the auditory outer and inner hair cells. That is, it was considered that the ototoxic hearing loss caused by GM may involve autophagy, and accordingly, it was deemed that the control of autophagy using the RPM may have an impact on hearing protection effects.

EXAMPLE 5

Observation of Autophagy Using Auditory Cell Line

To observe autophagy in the GM-treated auditory cells, the HEI-OC1 cells, which are the auditory cell line of Example 1-2, were subjected to immunohistochemistry using LC3 antibody, thereby staining autophagosomes, the expression of autophagy-related proteins, e.g., LC3, Beclin-1, and RAS-related GTP-binding proteins (Rab7) was confirmed according to the western blot, and the processes of autophagy were analyzed through real-time quantitative PCR. The observation results are shown in FIGS. 4A-4C.

Figure 4A:
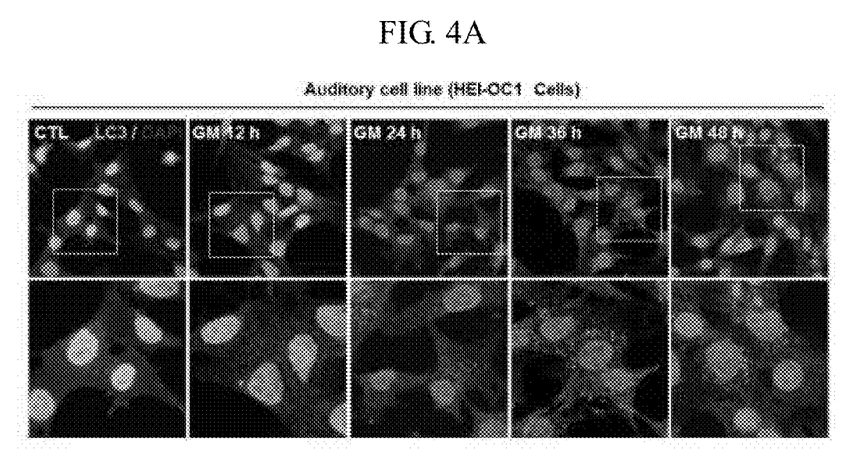
FIG. 4A shows images for observing autophagy in HEI-OC1 cells, which are auditory cell lines, after being treated with gentamicin.
Figure 4B:
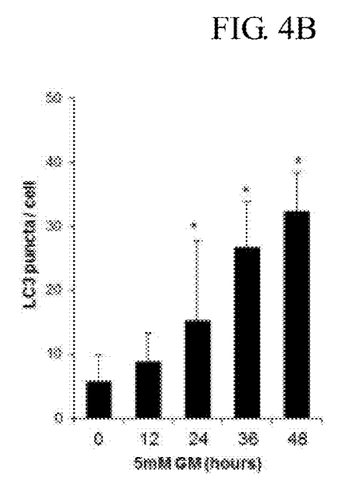
FIG. 4B and FIG. 4C show graph and images that are associated with expression of autophagy-related proteins.
Figure 4C:
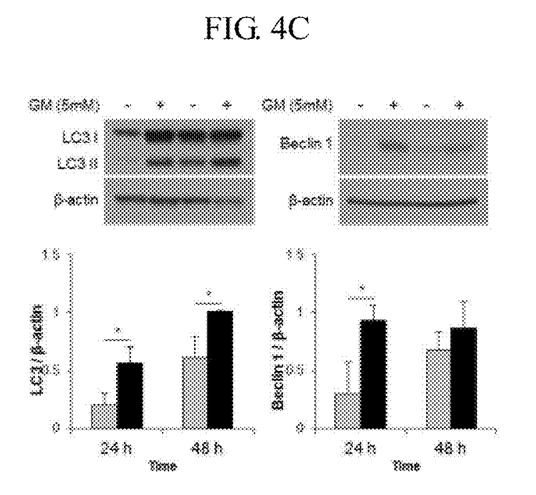

Referring to FIGS. 4A-4C, it was observed that, when the HEI-OC1 cells, which are the auditory cell line of Example 1-2, was treated with GM, the number of autophagosomes was increased over time. In addition, it was also observed that the expression of the autophagy-related proteins, e.g., LC3 and Beclin-1, was increased.

EXAMPLE 6

Analysis of RPM Effects on Apoptosis

To analyze effects of RPM on apoptosis, the HEI-OC1 cells, which are the auditory cell line of Example 1-2, were classified as follows, and then, extents of apoptosis thereof were analyzed according to the 3-(4,5-dimethylthiazol-2-yl)-5-(3-carboxymethoxyphenyl)-2-(4-sulfophenyl)-2H-tetraz olium (MTS assay). Here, RPM was used as an inducer of autophagy and chloroquine (CQ) was used as an inhibitor of autophagy in terms of pretreatment and combination treatment. The analysis results are shown in FIG. 5.

The classification of the HEI-OC1 cells was as follows: (1) normal cells (control group), (2) cells treated with RPM or CQ (3) cells treated with GM, and (4) cells treated with GM and RPM (or CQ) (wherein usage concentrations were as follows: 5 mM of GM, 20 nM of RPM, and 25 µM of CQ).

Figure 5:
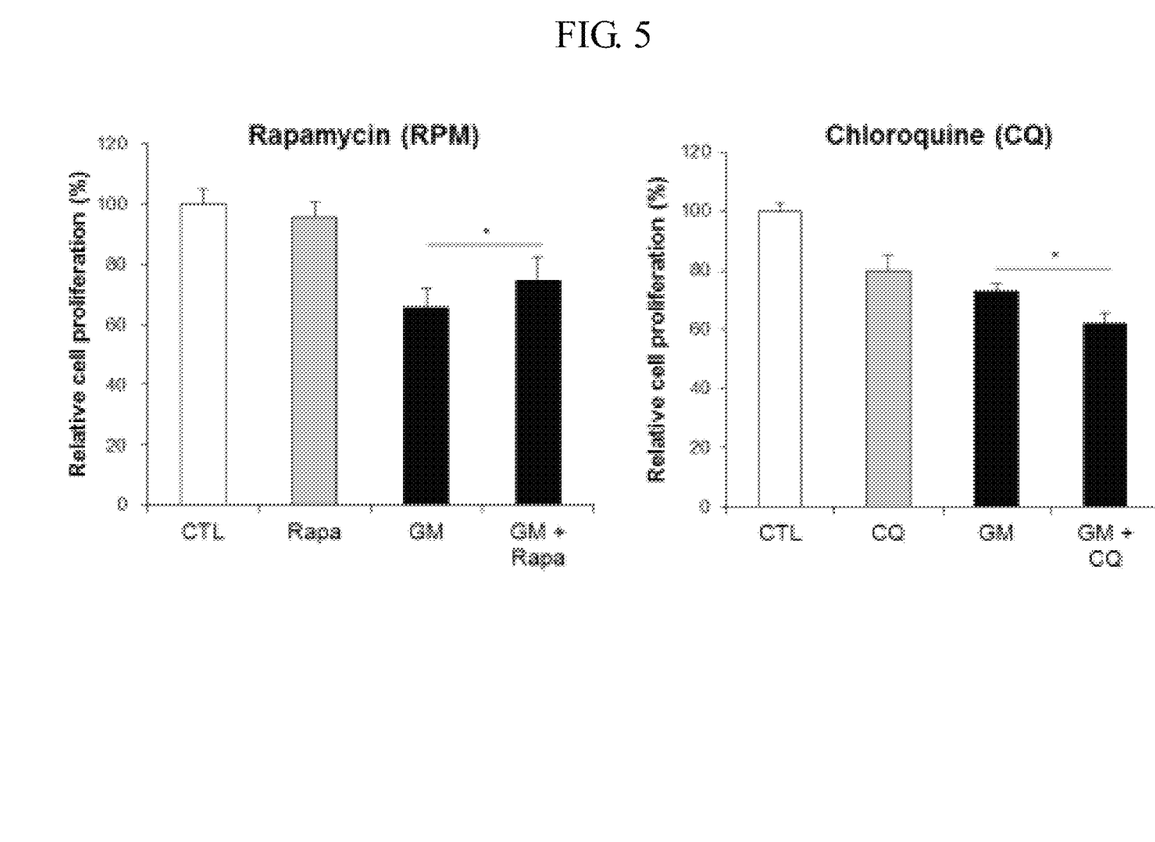
FIG. 5 shows graphs for observing apoptosis in HEI-OC1 cells, which are auditory cell lines, after being treated with gentamicin, a combination of gentamicin and rapamycin, or a combination of gentamicin and chloroquine.

Referring to FIG. 5, it was observed that, when the HEI-OC1 cells were treated with 5 mM of GM for 48 hours, about 25% of the HEI-OC1 cells were undergone the apoptosis. When the HEI-OC1 cells were treated with GM in combination with RPM, the HEI-OC1 cells were less likely to be undergone the apoptosis compared to the HEI-OC1 cells that were treated with GM only. Meanwhile, it was confirmed that, in the case where the HEI-OC1 cells were with the inhibitor of autophagy, CQ, the HEI-OC1 cells were more likely to be undergone the apoptosis.

Overall, it was confirmed that a combination use of GM and RPM, which are representative aminoglycoside-based antibiotics, leads to reduction in damage of the auditory cells and hearing loss.

In addition, in the case of the treatment using GM only, the number of autophagosomes each having a double membrane was increased in both auditory outer and inner hair cells, and accordingly, it was deemed that autophagy may be related to ototoxic hearing loss.

In addition, it was confirmed that the number of apoptosis was reduced in the case of the treatment using GM and RPM in combination while the number of apoptosis was increased in the case of the treatment using GM and CQ, which is the inhibitor of autophagy.

As described above, according to the one or more of the above exemplary embodiments, a pharmaceutical composition including rapamycin (RPM) as an active ingredient can be useful in the prevention or treatment of hearing loss selected from ototoxic hearing loss caused by an aminoglycoside-based antibiotic, sudden sensorineural hearing loss, and noise induced hearing loss.

In addition, according to the one or more of the above exemplary embodiments, a health food including RPM as an active ingredient can be useful in the prevention or treatment of hearing loss selected from the group consisting of ototoxic hearing loss caused by the aminoglycoside-based antibiotic, sudden sensorineural hearing loss, and noise induced hearing loss.

In addition, according to the one or more of the above exemplary embodiments, a pharmaceutical composite preparation of an aminoglycoside-based antibiotic and RPM can be used, wherein the pharmaceutical composite preparation is capable of reducing a side effect of the aminoglycoside-based antibiotic.

It should be understood that exemplary embodiments described herein should be considered in a descriptive sense only and not for purposes of limitation. Descriptions of features or aspects within each exemplary embodiment should typically be considered as available for other similar features or aspects in other exemplary embodiments.

While one or more exemplary embodiments have been described with reference to the figures, it will be understood by those of ordinary skill in the art that various changes in form and details may be made therein without departing from the spirit and scope as defined by the following claims.

What is claimed is:

1. A method of treating ototoxic hearing loss in a subject in need thereof, comprising:
   providing a pharmaceutical composition comprising a therapeutically effective amount of rapamycin as an active ingredient, wherein the therapeutically effective amount of the rapamycin is from 0.001 to about 100 mg/kg, and administered once or more a day; and
   administering the pharmaceutical composition to the subject, wherein the ototoxic hearing loss is treated,
   wherein the ototoxic hearing loss is caused by an aminoglycoside-based antibiotic.

2. The method of claim 1, wherein the aminoglycoside-based antibiotic is at least one selected from amikacin, arbekacin, gentamicin, kanamycin, neomycin, netilmicin, paromomycin, dibekacin, sisomicin, streptomycin, and tobramycin.

3. A method of treating ototoxic hearing loss in a subject in need thereof, comprising:
   providing a health food comprising a therapeutically effective amount of rapamycin as an active ingredient; and
   administering the health food to the subject, wherein the ototoxic hearing loss is treated,
   wherein the ototoxic hearing loss is caused by an aminoglycoside-based antibiotic.

4. The method of claim 3, wherein the aminoglycoside-based antibiotic is at least one selected from amikacin, arbekacin, gentamicin, kanamycin, neomycin, netilmicin, paromomycin, dibekacin, sisomicin, streptomycin, and tobramycin.

* * * * *